United States Patent
Antenucci et al.

(10) Patent No.: US 10,011,545 B2
(45) Date of Patent: Jul. 3, 2018

(54) PROCESS FOR THE MANUFACTURE OF α-IODOPERFLUOROALKANES AND α,ω-DIIODOPERFLUOROALKANES

(71) Applicant: SOLVAY SPECIALTY POLYMERS ITALY S.P.A., Bollate (IT)

(72) Inventors: Emanuela Antenucci, Saronno (IT); Letanzio Bragante, Due Carrare (IT); Marco Galimberti, Bollate (IT); Vito Tortelli, Milan (IT)

(73) Assignee: SOLVAY SPECIALTY POLYMERS ITALY S.P.A., Bollate (Milan) (IT)

( * ) Notice: Subject to any disclaimer, the term of this patent is extended or adjusted under 35 U.S.C. 154(b) by 0 days.

(21) Appl. No.: 15/303,474

(22) PCT Filed: Apr. 9, 2015

(86) PCT No.: PCT/EP2015/057655
§ 371 (c)(1),
(2) Date: Oct. 11, 2016

(87) PCT Pub. No.: WO2015/155264
PCT Pub. Date: Oct. 15, 2015

(65) Prior Publication Data
US 2017/0029349 A1     Feb. 2, 2017

(30) Foreign Application Priority Data
Apr. 11, 2014  (EP) .................................. 14164336

(51) Int. Cl.
C07C 17/272   (2006.01)
C07C 17/278   (2006.01)
C07C 19/16    (2006.01)
C07C 17/087   (2006.01)

(52) U.S. Cl.
CPC .......... *C07C 17/278* (2013.01); *C07C 17/087* (2013.01); *C07C 17/272* (2013.01); *Y02P 20/142* (2015.11)

(58) Field of Classification Search
CPC .... C07C 17/272; C07C 17/278; C07C 17/269
See application file for complete search history.

(56) References Cited

U.S. PATENT DOCUMENTS

| | | | |
|---|---|---|---|
| 3,404,189 A | 10/1968 | Blochl | |
| 3,523,140 A | 8/1970 | Cammarata et al. | |
| 3,644,544 A | 2/1972 | Cammarata et al. | |
| 4,861,845 A * | 8/1989 | Slocum ................. | C08F 14/18 526/231 |
| 4,922,041 A | 5/1990 | Naumann et al. | |
| 5,268,516 A | 12/1993 | Bertocchio et al. | |
| 5,345,013 A * | 9/1994 | Van Bramer .......... | C07C 17/42 570/102 |
| 7,071,367 B1 | 7/2006 | Mukhopadhyay et al. | |

FOREIGN PATENT DOCUMENTS

| | | |
|---|---|---|
| JP | 51133206 A | 11/1976 |
| JP | 53144507 A | 12/1978 |
| WO | 9429250 A1 | 12/1994 |
| WO | 9834967 A1 | 8/1998 |
| WO | 9919248 A1 | 4/1999 |

OTHER PUBLICATIONS

Tortelli V. et al., "Telomerization of tetrafluoroethylene and hexafluoropropene: synthesis of diiodoperfluoroalkanes", J. Fluorine Chem., 1990, vol. 47, p. 199-217.
"Ferrero F. et al., ""Analysis of the self-heating process of tetrafluoroethylene in a 100 dm3 reactor""", Journal of Loss Prevention in the Process Industries, 2012, vol. 25, Issue 6, p. 1010-1017—Elsevier Ltd."

* cited by examiner

*Primary Examiner* — Medhanit W Bahta

(57) ABSTRACT

The invention relates to a process for the manufacture of a-iodoperfluoroalkanes and α,ω-diiodoperfluoroalkanes of general formula: (1) $A(C_2F_4)_n I$, wherein: A is selected from F, $CF_3$ and I and n is an integer equal to or higher than 1, with the proviso that, when A is F, n is an integer higher than 1 said process comprising heating a mixture [mixture (M1)] containing: —a compound selected from $I_2$, $CF_3I$, $CF_3CF_2I$ and $C_2F_4I_2$; —TFE; —and $CO_2$ at definite temperatures and concentrations of $CO_2$.

19 Claims, No Drawings

PROCESS FOR THE MANUFACTURE OF α-IODOPERFLUOROALKANES AND α,ω-DIIODOPERFLUOROALKANES

CROSS-REFERENCE TO RELATED APPLICATIONS

This application is a U.S. national stage entry under 35 U.S.C. § 371 of International Application No. PCT/EP2015/057655 filed Apr. 9, 2015, which claims priority to European application No. 14164336.1, filed on Apr. 11, 2014. The entire contents of these applications are explicitly incorporated herein by this reference.

TECHNICAL FIELD

The present invention relates to a process for the manufacture of α-iodoperfluoroalkanes and α,ω-diiodoperfluoroalkanes.

BACKGROUND ART

α-Iodoperfluoroalkanes and α,ω-diiodoperfluoroalkanes (herein after otherwise respectively referred to as "I-telomers" and "$I_2$-telomers") are useful reagents or intermediates in a variety of applications.

α-Iodoperfluoroalkanes having general formula $F(CF_2)_nI$, wherein n is typically an integer higher than 3, can be used, for example, as intermediates for the manufacture of surfactants, pesticides, electronic materials or pharmaceuticals.

α,ω-Diiodoperfluoroalkanes having formula $I(C_2F_4)_nI$ (with n>1) such as, for example, 1,4-diiodoperfluorobutane ($C_4F_8I_2$) and 1,6-diiodoperfluorohexane ($C_6F_{12}I_2$), can be used as chain-transfer agents in polymerization reactions, as intermediates for the manufacture of other chemicals, including bis-olefins, diacids, polymers or for the manufacture of coatings.

α-Iodoperfluoroalkanes are typically synthesized by means of a telomerization reaction of TFE with a α-iodoperfluoroalkane, preferably $CF_3I$ or $CF_3CF_2I$. Usually, the most common and industrially convenient way to initiate the reaction is the heating of the starting reactants, the heating temperature being proportional to the length of the desired telomers. The reaction can be carried out in the liquid phase at a temperature of at least 150° C. under pressure. Alternatively, the reaction can be carried out at a temperature as high as 450° C. either at atmospheric pressure, thereby providing only a monoaddition I-telomer in a single step of the reaction, or under pressure, thereby giving rise to a broad distribution of telomers. Methods for the synthesis of I-telomers are disclosed, for instance, in U.S. Pat. No. 3,404,189 (FMC CORP) Jan. 10, 1968, U.S. Pat. No. 5,268,516 U.S. Pat. No. 5,268,516 (ATOCHEM ELF SA) and WO 99/19248 (DU PONT) Apr. 22, 1999.

α,ω-Diiodoperfluoroalkanes are typically synthesized by means of a process comprising the reaction of tetrafluoroethylene (TFE) with iodine in the presence of different initiators, at different temperatures. Also in this case, on an industrial scale it is preferred to initiate the reaction by heating the reactants. TFE promptly reacts with iodine to provide $C_2F_4I_2$, which is in equilibrium with TFE and iodine; $C_2F_4I_2$ further reacts with TFE to provide higher-length telomers.

JP S51133206 (ASAHI GLASS CO LTD) Nov. 18, 1976 discloses a process for the preparation of $I_2$-telomers of formula $I(C_2F_4)_nI$ (n=2-4) by thermal decomposition of $C_2F_4I_2$. The telomerization reaction of TFE with $C_2F_4I_2$ is disclosed in TORTELLI, et al. Telomerization of tetrafluoroethylene and hexafluoropropene: synthesis of diiodoperfluoroalkanes. *J. Fluorine Chem.* 1990, vol. 47, p. 199-210.

Example 29 of WO 98/34967 A (THE UNIVERSITY OF NORTH CAROLINA) Aug. 13, 1998 teaches to synthesize a low molecular weight polymer or oligomer [namely $CF_3(C_2F_4)_nI$ or $F(C_2F_4)_nI$] by irradiation of TFE with a UV lamp and heating at 36° C. in the presence of carbon dioxide and of a chain transfer agent such as $CF_3I$ or IF.

The main problem in the synthesis of I-telomers and $I_2$-telomers is the handling of TFE, which is flammable and explosive; flammability and explosivity increase with temperature and pressure. Therefore, in the course of the synthesis, it is necessary to properly control temperature and pressure in order not to go beyond critical values. Normally, if temperature is increased, pressure values must be controlled in such a way as not to go beyond 400 kPa at most. This has a negative impact on the productivity of the process. Indeed, under such conditions, less TFE is available in the liquid phase to react with $I_2$, which decreases the reaction speed. In principle, speed could be increased by increasing the TFE pressure or the temperature, but this is not possible due to safety concerns and to the occurrence of undesired side-reactions (i.e. formation of perfluorocyclobutane, TFE polymerization, formation of perfluoroalkanes and $I_2$). Furthermore, the Applicant has observed that reaction mixtures containing TFE and $I_2$, which form $C_2F_4I_2$ and higher length telomers, are even more flammable and explosive than TFE alone. This is quite surprising, as it was expected that $I_2$ present in such mixtures as a result of dissociation of $C_2F_4I_2$ and higher length telomers would act as a radical scavenger, thereby increasing the stability of the mixture. The same increased risk of flammability and explosivity is also associated to reaction mixtures containing TFE and $CF_3CF_2I$ used in the synthesis of α-iodoperfluoroalkanes, since they also give rise to a certain amount of $I_2$, which is known to react with TFE giving rise to $C_2F_4I_2$.

It is also well known (for example from FERRERO, Fabio, et al. Analysis of the self-heating process of tetrafluoroethylene in a 100-dm3-reactor. *Journal of Loss Prevention in the Process Industries.* 2012, vol. 25, no. 6, p. 1010-1017.) that a further major concern is represented by the MITD (minimum ignition temperature decomposition) of TFE which decreases by increasing pressure (it decreases from 260° C. at 500 kPa to 230° C. at 1,000 kPa).

EP 702666 A (DU PONT) discloses single-phase, liquid mixtures of TFE and $CO_2$ which are said to be characterised by reduced explosivity. This document focuses on the storage and transport of the mixtures and discloses only in broad terms that TFE/$CO_2$ mixtures can be used directly in TFE polymerization processes or as a diluent/heat sink in chemical reactions involving TFE. However, this document does not suggest any stabilizing effect of $CO_2$ on other systems other than TFE.

There is therefore the need to provide a process for the manufacture of α-iodoperfluoroalkanes and α,ω-diiodoperfluoroalkanes, said process having high productivity and, at the same time, increased safety.

An additional drawback encountered in the manufacture of I-telomers and I 2-telomers, e.g. $C_4F_9I$, $C_4F_8I_2$, $C_6F_{13}I$ and $C_6F_{12}I_2$, lies in the formation of an undesired side-product, perfluorocyclobutane (cy-$C_4F_8$), an inert gas having a boiling point of 6° C. The presence of this side-product in the reactor decreases the reaction speed. In order to overcome this drawback, it is necessary to purge the reactor, so as to remove cy-$C_4F_8$, and add further TFE. However, by doing this, not only cy-$C_4F_8$ is discharged from the reactor, but also TFE.

JP S53144507 (ASAHI GLASS CO LTD) discloses the preparation of 1,4-diiodo perfluorobutane by thermal decomposition of $C_2F_4I_2$ in the presence of $I_2$ and an inert gas. The inert gas has the effect of reducing the amount of cy-$C_4F_8$ formed in the course of the process. The sole inert gas mentioned in this document is nitrogen.

It would thus be desirable to provide a further, safe process for the manufacture of α-iodoperfluoroalkanes and α,ω-diiodoperfluoroalkanes also allowing to keep to a minimum the amount of cy-$C_4F_8$ formed in the reaction. It would also be desirable to provide a process that allows achieving a high productivity of telomers, in particular those having a low molecular weight.

SUMMARY OF INVENTION

The applicant has now found out that α-iodoperfluoroalkanes and α,ω-diiodoperfluoroalkanes of general formula:

$$A(C_2F_4)_nI, \quad (I)$$

wherein:
A is selected from F, $CF_3$ and I and
n is an integer equal to or higher than 1, with the proviso that, when A is F,
n is an integer higher than 1 can be conveniently manufactured by means of a process (or "method") which comprises heating a mixture [mixture (M1)] containing:
   a compound selected from $I_2$, $CF_3I$, $CF_3CF_2I$ and $C_2F_4I_2$;
   TFE;
   and $CO_2$ at a temperature equal to or higher than 130° C., said mixture comprising a liquid phase and a gas phase and containing $CO_2$ in an amount of at least 18% vol with respect to the gas phase.

It has indeed been found out that the heating of mixture (M1) at a temperature equal to or higher than 130° C. in the presence of $CO_2$ in an amount of at least 18% vol, preferably of at least 20% vol, provides advantages in terms of safety, because, in case of accidental ignition of the gas phase, there is a relevant mitigation of the maximum pressure reached in the reactor.

It has also been found out that the heating of mixture (M1) at a temperature equal to or higher than 130° C. in the presence of $CO_2$ in an amount of at least 27% provides an additional advantage, since the mixture of reaction products obtained from mixture (M1) in the course of the process is not explosive.

Preferably, in formula (I) above, A is selected from F and I and n is an integer higher than 1. More preferably, n ranges from 2 to 4; this range is preferred in all preferred embodiments indicated below.

For the sake of clarity, when ranges are indicated in the present description, range ends are always included.

Thus, in a first embodiment, the process allows obtaining α-iodoperfluoroalkanes of formula (Ia):

$$A(C_2F_4)_nI \quad (Ia)$$

wherein A is F or $CF_3$ and n is an integer equal to or higher than 1, with the proviso that, when A is F, n is an integer higher than 1. Preferably, the process allows obtaining α-iodoperfluoroalkanes (Ia*) wherein A is F and n is an integer higher than 1.

In a second embodiment, the process allows obtaining α,ω-iodoperfluoroalkanes of formula:

$$I(C_2F_4)_nI \quad (Ib)$$

wherein n is an integer equal to or higher than 1, preferably higher than 1.

Manufacture of α-iodoperfluoroalkanes

The manufacture of α-iodoperfluoroalkanes of formula (Ia) as defined above according to the present invention is typically carried out at temperatures ranging from 130° C. to 500° C., the two following embodiments being preferred.

Process (A)

According to a first preferred embodiment [herein after "process (A)"], the manufacture of α-iodoperfluoroalkanes of formula (Ia) is carried out by heating a mixture (Mia) containing $CF_3I$ or $CF_3CF_2I$, TFE and $CO_2$ at a temperature ranging from 170° C. to 250° C., preferably from 190° C. to 220° C., while feeding TFE and $CO_2$ in the course of the process. Typically, $CF_3I$ or $CF_3CF_2I$ are charged in the reactor, the temperature is raised up to 170° C.-250° C., preferably up to 190° C.-220° C., and TFE and $CO_2$ are fed in the reactor in the course of the process.

$CF_3I$ and $CF_3CF_2I$ can be manufactured according to methods known in the art, for example as disclosed in U.S. Pat. No. 3,523,140 (MONTEDISON S.P.A.) Aug. 4, 1970, U.S. Pat. No. 3,644,544 (MONTEDISON S.P.A.) Feb. 22, 1972, U.S. Pat. No. 4,922,041 (KALI CHEMIE AG) May 1, 1990, and U.S. Pat. No. 7,071,367 (HONEYWELL INT INC) Jun. 15, 2006.

Typically, TFE is added in a molar amount ranging from 0.5 to 3.0 with respect to $CF_3I$ or $CF_3CF_2I$.

The process is typically carried out for a time ranging from 1 to 12 hours, preferably from 1 to 24 hours, more preferably from 1 to 48 hours.

In any case, the amount of TFE and the reaction time will be adjusted by the skilled person according to the length of the desired telomer; the longer the reaction time and the higher the TFE amount, the higher the length of the desired telomer. The formation of the desired telomer can be monitored on withdrawn samples according to known methods.

The amount of $CO_2$ is of at least 18%, preferably of at least 20%, more preferably of at least 27% with respect to the gas phase.

In the course of the process, the pressure in the reactor is monitored and is not allowed to go beyond 2,500 kPa by purging the reactor. Purging the reactor allows removing any cy-$C_4F_8$ formed in the course of the reaction.

Process (B)

According to a second preferred embodiment [herein after "process (B)"], the manufacture of α-iodoperfluoroalkanes of formula (Ia) is carried out by heating a mixture (M1a) containing $CF_3I$ or $CF_3CF_2I$, TFE and $CO_2$ at a temperature ranging from 300° C. to 500° C., preferably from 350° C. to 450° C. Typically, $CF_3I$ or $CF_3CF_2I$ are pumped in the reactor at temperature ranging from 300° C. to 500° C., preferably from 350° C. to 450° C., while TFE and $CO_2$ are fed in the reactor in the course of the process.

Typically, TFE is added in a molar amount ranging from 0.5 to 3, more preferably from 0.5 to 1 with respect to $CF_3I$ or $CF_3CF_2I$. Also in this case, the amount of TFE and the reaction time will be adjusted by the skilled person according to the length of the desired telomer.

The amount of $CO_2$ is of at least 18%, preferably of at least 20%, more preferably of at least 27% with respect to the gas phase.

In the course of the process, the pressure in the reactor is monitored and typically kept within a range of 100 kPa and 1,000 kPa.

Usually, both in process (A) and (B), one or more α-iodoperfluoroalkanes (Ia)—typically $C_4F_9I$ and/or $C_6F_{13}I$ in the manufacture of α-iodoperfluoroalkanes (Ia*)—is/are obtained as a mixture (M2a) with unreacted $CF_3I$ or $CF_3OF_2I$, TFE and with any $C_2F_4I_2$ and $I_2$ possibly formed in the course of the reaction. Mixture (M2a) may further contain cy-$C_4F_8$ and/or dimeric perfluoroalkanes. The one or more α-iodoperfluoroalkanes of formula (Ia) or (Ia*) can be isolated by fractionation techniques according to methods known in the art.

Manufacture of α,ω-iodoperfluoroalkanes

The manufacture of a α,ω-iodoperfluoroalkane of formula:

(Ib)

wherein n is 1
(1,2-diiodotetrafluoroethane)
according to the present invention is typically carried out by contacting $I_2$ with TFE and heating at a temperature ranging from 130° C. to 170° C. in the presence of an amount of $CO_2$ of at least 18%, preferably of at least 20%, more preferably of at least 27% with respect to the gas phase.

The reaction is typically carried out for a time ranging from 1 hr to 6 hrs, preferably from 1 hr to 4 hrs, more preferably from 1 hr to 2 hrs. TFE and $I_2$ are typically used in a molar ratio of about 1:1.

The manufacture of α,ω-iodoperfluoroalkanes of formula:

(Ib)

wherein n is an integer higher than 1
according to the invention is typically carried out according to the two following embodiments.

In a first embodiment [herein after "process (C)"], a mixture (M1b) comprising $C_2F_4I_2$, TFE and $CO_2$ is heated to a temperature ranging from 170° C. to 250° C., preferably of 200° C., while feeding TFE and $CO_2$ in the course of the process. Typically, $C_2F_4I_2$ is fed in the reactor, heated to 170° C.-250° C., preferably at 200° C., and TFE and $CO_2$ are fed in the reactor in the course of the process.

In a second embodiment [herein after "process (D)"], the heating of mixture (M1b) is carried out at a temperature in the range of 170° C.-280° C. in the presence of $CO_2$, without feeding TFE in the course of the process.

Mixture (M1b) is typically prepared by contacting TFE with $I_2$ in the presence of $CO_2$, followed by heating at a temperature of 130° C., to provide a mixture [mixture (M1b)] comprising $C_2F_4I_2$, TFE and $I_2$. Mixture (M1b) can be directly subjected to the process or can be submitted to a purification step in order to reduce the amount of $I_2$ and TFE therein contained. The purification step can be carried out according to known methods.

Process (C)

Typically, process (C) comprises the following steps:
(a1) reacting TFE with $I_2$ in the presence of $CO_2$ at a temperature of 130° C. to provide a mixture (M1b) of $C_2F_4I_2$, TFE and $I_2$;
(a1*) optionally purifying mixture (M1b) to reduce the amount of $I_2$ and TFE therein contained;
(a2) heating mixture (M1b) at a temperature ranging from 170° C. to 250° C., preferably of 200° C., while feeding TFE and $CO_2$.

Step (a1) is typically carried out for a time ranging from 1 hr to 6 hrs, preferably from 1 hr to 4 hrs, more preferably from 1 hr to 2 hrs. In step (a1), TFE and $I_2$ are typically used in a molar ratio of about 1:1.

Step (a2) is typically carried out for a time ranging from 1 hr to 12 hrs, preferably from 1 hr to 24 hrs, more preferably from 1 hr to 48 hrs. In this step, TFE is added at a pressure ranging from 1,000 to 3,500 kPa. The reaction time and the TFE pressure will be adjusted by the person skilled in the art according to the length of the desired telomer; the longer the reaction time and the higher the TFE pressure, the higher the length of the desired telomer. The formation of the desired telomer can be monitored on withdrawn samples according to known methods.

The amount of $CO_2$ fed in the reactor in steps (a1) and (a2) is of at least 18% vol, preferably of at least 20% vol, more preferably of at least 27% vol with respect to the gas phase of mixture (M1b).

During step (a2), the pressure in the reactor is monitored and kept at values not beyond 2,500 kPa by purging the reactor. Purging the reactor allows removing any cy-$C_4F_8$ formed in the course of the reaction.

Usually, at the end of step (a2), one or more α,ω-diiodoperfluoroalkanes of formula (I), typically $C_4F_8I_2$ and/or $C_6F_{12}I_2$, is/are obtained as a mixture [mixture (M2b)] with unreacted $C_2F_4I_2$ and also with TFE and $I_2$ formed by dissociation of $C_2F_4I_2$. More typically, more α,ω-diiodoperfluoroalkanes of formula (Ib) are obtained in admixture with unreacted $C_2F_4I_2$, TFE and $I_2$. Mixture (M2b) usually contains cy-$C_4F_8$ as by-product. The one or more α,ω-diiodoperfluoroalkane of formula (Ib) can thus be isolated by submitting mixture (M2b) to a purification step. This purification step can be carried out according to known methods, for example as disclosed in JP S51133206 (ASAHI GLASS CO LTD) Nov. 18, 1976.

Process (D)

Process (D) typically comprises the following steps:
(b1) reacting TFE with $I_2$ in the presence of $CO_2$ at a temperature of 130° C. to provide a mixture (M1b) of $C_2F_4I_2$, TFE and $I_2$;
(b1*) optionally purifying mixture (M1b) to reduce the amount of $I_2$ and TFE therein contained;
(b2) heating mixture (M1b) at a temperature ranging from 170° C. to 280° C., preferably from 200° C. to 250° C., more preferably from 230° C. to 250° C. in the presence of $CO_2$, without feeding TFE.

The reaction time and reagent amounts to be used in step (b1) are the same as in step (a1).

Step (b2) is typically carried out for a time ranging from 1.5 hr to 24 hrs.

The amount of $CO_2$ fed in the reactor in steps (b1) and (b2) is of at least 18% vol, preferably of at least 20% vol, more preferably of at least 27% vol with respect to the gas phase of mixture (M1b).

Process (D) may advantageously comprise an additional step (b2*) which comprises reducing the temperature to 130° C. and adding TFE, typically in an amount ranging from 10% to 25% wt with respect to the amount of $C_2F_4I_2$ in mixture (M1b) before step (b2), in order to quench $I_2$ formed in the reaction.

Similarly to step (a2), at the end of step (b2) or (b2*), one or more α,ω-diiodoperfluoroalkanes of formula (Ib), typically $C_4F_8I_2$ and/or $C_6F_{12}I_2$, is/are obtained as a mixture [mixture (M2b)] with unreacted $C_2F_4I_2$ and also with TFE and $I_2$ formed by dissociation of $C_2F_4I_2$. More typically, more α,ω-diiodoperfluoroalkanes of formula (Ib) are obtained in admixture with unreacted $C_2F_4I_2$ and also with TFE and $I_2$ in equilibrium with $C_2F_4I_2$. Mixture (M2b) may also contain cy-$C_4F_8$ as by-product. The one or more α,ω-diiodoperfluoroalkane of formula (Ib) can be thus isolated by submitting mixture (M2b) to a purification step. This purification step can be carried out according to known methods, for example as disclosed in JP S51133206 (ASAHI GLASS CO LTD) Nov. 18, 1976.

Product fractions obtained from the purification step that contain $C_2F_4I_2$ and higher length telomers can be conveniently recovered and be re-cycled to steps (a2) or (b2) of process (C) or (D) respectively; thus, such fractions can be used as alternatives or in addition to a mixture (M1b) in these embodiments of the invention.

As stated above, the presence of $CO_2$ in an amount of at least 18% vol, preferably of at least 20% vol, allows increasing the safety of the process, because it has a stabilizing effect on the mixture of products formed in the course of the reaction, in particular on mixtures of $C_2F_4$ and $C_2F_4I_2$. More specifically, it has been observed that an amount of at least 18% vol, preferably of at least 20% vol, mitigates the maximum pressure reached in the reactor, while an amount of at least 27% allows avoiding the risk of explosion.

With respect to process (C), process (D) provides a further advantage, which is that of reducing the amount of undesired cy-$C_4F_8$ that forms as by-product. While in process (C) an overall weight amount of cy-$C_4F_8$ typically in the range of 35% to 40% with respect to mixture (M2b) is obtained, in process (D) the amount of this side product is below 20%. Process (D) is further advantageous in that purging the reactor during step (b2) is not required, which makes the process less troublesome and avoids losses of $CO_2$ and TFE.

The invention and its advantages will be herein after illustrated in greater detail in the following experimental section and non-limiting examples.

Should the disclosure of any patents, patent applications, and publications which are incorporated herein by reference conflict with the description of the present application to the extent that it may render a term unclear, the present description shall take precedence.

EXPERIMENTAL SECTION

Material and Methods

1. General Procedure for Process (C)

A mixture (M1b) containing a definite amount of $C_2F_4I_2$ was introduced in a stainless steel reactor and the temperature was raised to 200° C.; thereafter, a TFE and $CO_2$ mixture (80:20 by vol) was fed in continuous in the reactor. Pressure was adjusted at 2,500 kPa by purging the reactor. At the end of the reaction, the reactor was cooled down to room temperature and discharged. In the course of the process, cy-$C_4F_8$, TFE and $CO_2$ were purged from the reactor and not recovered.

2. General Procedure for Process (D)

A mixture (M1b) containing a definite amount of $C_2F_4I_2$ was introduced in a stainless steel reactor and uncondensable substances were evacuated after having cooled the reactor with dry-ice. The temperature was raised to 50° C. and the pressure was equilibrated to 530 kPa with $CO_2$ while stirring. Thereafter, the temperature was raised to 235° C., while pressure rose up to 3,000 kPa, and heating was continued until the composition of withdrawn samples revealed an amount of $CO_2$ of at least 30% vol (about 3 hrs).

At this stage, the temperature was lowered to 130° C. and TFE was added keeping the reactor at a maximum pressure of 1,500 kPa. Thereafter, the reactor was cooled down to room temperature, purged and discharged.

3. Stability Test

The explosivity of TFE, $C_2F_4I_2$ and $C_4F_8I_2$ and of TFE/ $C_2F_4I_2$ mixtures was evaluated by measuring the pressure at explosion.

The test was performed in a vertically mounted stainless steel autoclave (0.34 L volume and 48 mm diameter).

Pressure at explosion was measured by means of a quick response pressure transducer (oscillation frequency of the membrane of 10 kHz minimum), an electronic transducer and a cathode-beam oscillograph. The pressure transducer was mounted on top of the autoclave.

An ignitor was installed at a distance of 20-30 mm from the bottom of the autoclave close to the symmetry axis. A nichrome wire (diameter: 0.25 mm; length; 4-6 mm), fused by applying a 150V, was used as the ignitor.

An electrically heated nichrome wire spiral (spiral diameter: 10-12 mm; nichrome wire diameter: 1.1 mm; number of turns: 11; spiral length: 30-35 mm) was installed at the bottom of the autoclave in order to intensify convection when mixing the tested compounds or mixtures.

Synthesis Examples and Results of Stability Tests

Examples 1 and 2 [Process (C)]

Following the procedure disclosed at point 1 of the section "Material and methods", Examples 1 and 2 were carried out in a 0.6 L stainless steel reactor with the amounts of reagents and conditions reported in Table 1 below.

TABLE 1

| Example | C2F4I2* | TFE | CO2 | Reaction time (hrs) |
|---------|---------|-------|-------|---------------------|
| 1 | 1,080 g | 505 g | 132 g | 47 hrs |
| 2 | 797 g | 434 g | 98 g | 44 hrs |

*initial amount of $C_2F_4I_2$ in mixture (M1b).

At the end of the reaction, mixtures (M2b) were obtained with the compositions reported in Table 2 below.

TABLE 2

| Example | C2F4I2 | C4F8I2 | C6F12I2 | C8F16I2 | cy-C4F8 |
|---------|--------|--------|---------|---------|---------|
| 1 | 621 g | 365 g | 137 g | 15 g | 148 g |
| 2 | 588 g | 189 g | 96 g | 12 g | 131 g |

Examples 3 and 4 [Process (D)]

Following the procedure disclosed at point 2 of the section "Material and methods", Examples 3 and 4 were carried out in a 0.6 L stainless steel reactor with the amounts of reagents and conditions reported in Table 3 below.

TABLE 3

| Example | C2F4I2 | CO2 | Reaction time (hrs)** | TFE (amount and addition time) |
|---------|--------|------|-----------------------|--------------------------------|
| 3 | 715 g | 12 g | 6.5 | 108 g (4 hrs) |
| 4 | 731 g | 12 g | 14.5 | 120 g (4 hrs) |

*initial amount of $C_2F_4I_2$ in mixture (M1b)
* time of reaction is referred to the end of the heating at 235° C.

At the end of the reaction, mixtures (M2b) were obtained with the compositions reported in Table 4 below.

TABLE 4

| Example | C2F4I2 | C4F8I2 | C6F12I2 | C8F16I2 | cy-C4F8 |
|---|---|---|---|---|---|
| 3 | 596 g | 128 g | 23 g | 0.3 g | 12 g |
| 4 | 586 g | 154 g | 37 g | 4 g | 18 g |

Results of Stability Tests

Table 5 below reports the results of stability tests carried out on TFE alone and on mixtures of TFE with $C_2F_4I_2$ or $C_4F_8I_2$ at different initial temperatures and pressures ($P_0$) in the absence of $CO_2$. The results are expressed as the ratio between the maximum pressure reached after ignition ($P_{max}$) and $P_0$. For $P_{max}/P_0$ ratios lower than or equal to 1.1 the compound or the mixture is considered stable and not exploding.

The results show (see in particular entries 13-15 compared to entry 3) that mixtures of TFE and $C_2F_4I_2$ have a higher $P_{max}/P_0$ ratio than TFE, so they are less safe than TFE alone. The same result was obtained with mixtures of TFE and $C_4F_8I_2$ (see in particular entry 6).

TABLE 5

| N° of test | $P_0$ (KPa) | $T_0$ (° C.) | Concentration (% vol) | | | $P_{max}/P_0$ |
|---|---|---|---|---|---|---|
| | | | TFE | $C_2F_4I_2$ | $C_4F_8I_2$ | |
| 1 | 1,500 | 200 | 100 | / | / | 4.95 |
| 2 | 2,000 | 200 | 100 | / | / | 5.1 |
| 3 | 2,500 | 200 | 100 | / | / | 5.35 |
| 4 | 1,500 | 200 | 90 | / | 10 | 5.5 |
| 5 | 2,000 | 200 | 92.5 | / | 7.5 | 5.7 |
| 6 | 2,500 | 200 | 94 | / | 6 | 6.5 |
| 7 | 1,500 | 200 | 45 | 55 | / | 5.9 |
| 8 | 1,500 | 200 | 95 | 5 | / | 5.7 |
| 9 | 1,500 | 200 | 90 | 10 | / | 5.8 |
| 10 | 2,000 | 200 | 59 | 41 | / | 6.8 |
| 11 | 2,000 | 200 | 90 | 10 | / | 6.8 |
| 12 | 2,000 | 200 | 95 | 5 | / | 6.5 |
| 13 | 2,500 | 200 | 67 | 33 | / | 6.9 |
| 14 | 2,500 | 200 | 90 | 10 | / | 6.9 |
| 15 | 2,500 | 200 | 95 | 5 | / | 6.7 |

Table 6 below reports instead the results of stability tests carried out on mixtures of TFE and $C_2F_4I_2$ at different pressures $P_0$ and at different concentrations of $CO_2$.

TABLE 6

| N° of test | $P_0$ (KPa) | $T_0$ (° C.) | Concentration (% vol) | | | $P_{max}/P_0$ |
|---|---|---|---|---|---|---|
| | | | TFE | $C_2F_4I_2$ | $CO_2$ | |
| 1 | 1,500 | 200 | 85.5 | 5 | 9.5 | 5.6 |
| 2 | 1,500 | 200 | 76 | 5 | 19 | 1.4 |
| 3 | 1,500 | 200 | 66.5 | 5 | 28.5 | 1 |
| 4 | 2,500 | 200 | 85.5 | 5 | 9.5 | 6.7 |
| 5 | 2,500 | 200 | 76 | 5 | 19 | 1.8 |
| 6 | 2,500 | 200 | 66.5 | 5 | 28.5 | 1 |
| 7 | 2,500 | 200 | 81 | 10 | 9 | 6.5 |
| 8 | 2,500 | 200 | 72 | 10 | 18 | 2 |
| 9 | 2,500 | 200 | 63 | 10 | 27 | 1 |
| 10 | 2,500 | 200 | 40 | 33 | 27 | 1 |
| 11 | 2,500 | 200 | 18 | 55 | 27 | 1 |

The results show that, when the concentration of $CO_2$ in the mixture is 18% vol, the $P_{max}/P_0$ value is significantly lower. The results further show that, when the concentration of $CO_2$ in the mixture is 27% vol, no explosion occurs.

The invention claimed is:

1. A process for the manufacture of at least one compound of general formula (I):

$$A(C_2F_4)I \quad (I)$$

wherein:
A is selected from the group consisting of F, $CF_3$ and I and
n is an integer equal to or higher than 1, with the proviso that, when A is F, n is an integer higher than 1 said process comprising heating a mixture (M1) containing:
a compound selected from the group consisting of $I_2$, $CF_3I$, $CF_3CF_2I$ and $C_2F_4I_2$;
tetrafluoroethylene (TFE); and
$CO_2$ at a temperature equal to or higher than 130° C., said mixture comprising a liquid phase and a gas phase and containing $CO_2$ in an amount of at least 18% vol with respect to the gas phase.

2. The process according to claim 1, wherein the amount of $CO_2$ is of at least 20%.

3. The process according to claim 2, wherein the amount of $CO_2$ is of at least 27%.

4. The process according to claim 1, wherein the at least one compound of general formula (I) is at least one α-iodoperfluoroalkane of formula (Ia):

$$A(C_2F_4)I \quad (Ia)$$

wherein A is F or $CF_3$ and n is an integer equal to or higher than 1, with the proviso that, when A is F, n is an integer higher than 1.

5. The process according to claim 4, said process comprising heating a mixture (M1a) containing $CF_3I$ or $CF_3CF_2I$, TFE and $CO_2$ at a temperature ranging from 170° C. to 250° C., while feeding TFE and $CO_2$ in the course of the process.

6. The process according to claim 4, said process comprising heating a mixture (M1a) containing $CF_3I$ or $CF_3CF_2I$, TFE and $CO_2$ at a temperature ranging from 300° C. to 500° C., while feeding TFE and $CO_2$ in the course of the process.

7. The process according to claim 4, wherein the amount of $CO_2$ is of at least 20%.

8. The process according to claim 7, wherein the amount of $CO_2$ is of at least 27%.

9. The process according to claim 1, wherein the at least one compound of general formula (I) is an α,ω-diiodoperfluoroalkane of formula (Ib):

$$A(C_2F_4)_nI \quad (Ib)$$

wherein A is I and n is 1, and wherein said process is carried out by contacting $I_2$ with TFE and heating at a temperature ranging from 130° C. to 170° C.

10. The process according to claim 9, wherein the amount of $CO_2$ is of at least 20%.

11. The process according to claim 10, wherein the amount of $CO_2$ is of at least 27%.

12. The process according to claim 1, wherein the at least one compound of general formula (I) is at least one α,ω-diiodoperfluoroalkane of formula (Ib):

$$A(C_2F_4)_nI \quad (Ib)$$

wherein A is I and n is an integer higher than 1.

13. The process according to claim 12, said process comprising heating a mixture (M1b) comprising $C_2F_4I_2$, TFE and $CO_2$ at a temperature ranging from 170° C. to 250° C., while feeding TFE and $CO_2$ in the course of the process.

14. The process according to claim 13 which comprises the following steps:

(a1) reacting TFE with $I_2$ in the presence of $CO_2$ at a temperature of 130° C. to provide a mixture (M1b) of $C_2F_4I_2$, TFE and iodine;

(a1*) optionally purifying mixture (M1a) to reduce the amount of $I_2$ and TFE therein contained;

(a2) heating mixture (M1b) at a temperature ranging from 170° C. to 250° C. while feeding TFE and $CO_2$ in the course of the process.

15. The process according to claim 12, said process comprising heating of a mixture (M1b) comprising $C_2F_4I_2$, TFE and $CO_2$ at a temperature ranging from 170° C. to 280° C. in the presence of $CO_2$, without feeding TFE in the course of the process.

16. The process according to claim 15 which comprises the following steps:

(b1) reacting TFE with $I_2$ in the presence of $CO_2$ at a temperature of 130° C. to provide a mixture (M1b) of $C_2F_4I_2$, TFE and iodine;

(b1*) optionally purifying mixture (M1b) to reduce the amount of $I_2$ and TFE therein contained;

(b2) heating mixture (M1) at a temperature ranging from 170° C. to 280° C. in the presence of $CO_2$, without feeding TFE in the course of the process.

17. The process according to claim 16, wherein step (b2) is carried out at a temperature ranging from 200° C. to 250° C.

18. The process according to claim 17, wherein step (b2) is carried out at a temperature ranging from 230° C. to 250° C.

19. The process according to claim 16, further comprising a step (b2*) after step (b2), wherein step (b2*) comprises reducing the temperature to 130° C. and adding TFE in an amount ranging from 10% to 25% wt, wherein the % wt of TFE is calculated with respect to the amount of $C_2F_4I_2$ in mixture (M1b) before step (b2).

* * * * *